United States Patent
Hammons et al.

[11] Patent Number: 5,840,246
[45] Date of Patent: Nov. 24, 1998

[54] OIL LAMP WITH FRAGRANCE EMANATOR

[75] Inventors: Randall Lee Hammons, Sussex; Stephen Vito Dente, Tenafly; Thomas Shiaw-tong Lin, Whippany, all of N.J.

[73] Assignee: Reckitt & Colman Inc., Montvale, N.J.

[21] Appl. No.: 689,337

[22] Filed: Aug. 6, 1996

[30] Foreign Application Priority Data

Jun. 21, 1996 [GB] United Kingdom .................. 9613015

[51] Int. Cl.⁶ .............................. A61L 9/00; A62B 7/08
[52] U.S. Cl. .................... 422/4; 239/54; 239/55; 239/60; 422/1; 422/5; 422/122; 422/125
[58] Field of Search .............................. 422/1, 4, 5, 120, 422/122, 125; 239/54, 55, 60

[56] References Cited

U.S. PATENT DOCUMENTS

| | | | |
|---|---|---|---|
| 2,535,802 | 12/1950 | Libson | 422/125 |
| 2,539,696 | 1/1951 | Morrison | 422/125 |
| 3,898,039 | 8/1975 | Lin | 422/125 |
| 4,477,414 | 10/1984 | Muramoto et al. | 422/125 |
| 4,781,895 | 11/1988 | Spector | 422/125 |
| 4,892,711 | 1/1990 | Tendick, Sr. | 422/125 |

FOREIGN PATENT DOCUMENTS

| | | |
|---|---|---|
| 0277875 | 8/1988 | European Pat. Off. . |
| 204822 | 8/1922 | United Kingdom . |
| 249364 | 5/1925 | United Kingdom . |
| 253124 | 6/1926 | United Kingdom . |

Primary Examiner—Krisanne Thornton
Attorney, Agent, or Firm—Fish & Richardson P.C.

[57] ABSTRACT

A fragrance device for delivering a fragrance or other volatile material includes a fluid vessel containing a quantity of a fuel, a wick, and a porous emanator element which releases the fragrance or volatile material particularly when the wick is burning. Methods for the manufacture of the device, as well as methods for its use of are also disclosed.

25 Claims, 7 Drawing Sheets

OIL LAMP WITH FRAGRANCE EMANATOR

BACKGROUND OF THE INVENTION

Devices which utilize flame as a heat source and/or a vaporizing source for a fragrance are well known. These include candles, oil lamps which include scented oils, and other similar devices. In use such devices emanate a fragrance as a result of the heating of the oil or wax, and volatilization of a fragrance material which may be incorporated into the oil or wax.

In more detail, solid candle type air fresheners include a candle wax which may be dosed with one or more materials which emanate a fragrance when the candle is burned. These materials include for example herbs, fragrances and perfumes which may be derived from natural materials or ones which are synthetically produced, as well as other known materials. Such solid candle type devices are typically available at a low cost, are attractive in use and are popular in that they also generate a certain relaxed mood by the combination of the candlelight and fragrance. Such solid candles may be formed into any of a variety of shapes and forms, and may be used alone, or in conjunction with a containing vessel such as a candle holder which too may take any of a variety of shapes and forms. In operation, the unignited solid wax candles may emanate a fragrance, but their primary fragrancing operation occurs when they are burned. When ignited and burning, such candles generate a melted wax pool which allows for the volatilization and evaporation of the fragrance components which are included in their composition without such fragrance components being consumed to fuel the candle's flame. Preferred designs for such a standard solid candle includes a wax base which is contained in a glass or other inflammable container which is suited to contain the melted wax pool during the melting of the candle. Preferably, a wide-mouth design is used as such maximizes the melt surface of the melted wax pool and concomitantly provides a good fragrance delivery. However, such solid wax candles are not without their drawbacks some of which include: loss of the fragrance due to consumption with the wax fuel during burning; inconsistent or variable fragrance delivery due to the largely uncontrollable amount of melted wax and/or variable surface area of the wax pool occurring during various stages of the candles useful life; relatively short product life due to the inability of replenishing or refilling the candle unit; as well as the inability to change to change fragrance for the life of the solid wax candle. This latter most consideration is significant especially in view of many such prior art devices which may burn for 40 hours and even more in some cases.

Also known to the art, as has been briefly mentioned above, are oil lamps which contain a quantity of a fragranced lamp oil. Such a lamp oil is generally fueled by a hydrocarbon based material which includes within it a generally small quantity of a volatilizable fragrance material dispersed within. In use, when the wick is ignited, the flow of the fuel which includes the volatilizable material, i.e. fragrance, provides a fuel source for the continued burning. However, the fragrancing benefit of such an oil lamp is limited as, at the same time such burning generally consumes the hydrocarbon fuel as well as the fragrance oil, with the net effect of releasing little or no fragrance to the environment. Notwithstanding this shortcoming, such oil lamps remain popular as they are attractive in use, are generally available at a low cost, and are refillable with different fragranced oils thus imparting a long useful product life to such oil lamps.

Thus, there is a real and continued need in the art for the production of new fragrance delivery systems which utilize a flame.

There is a further need in the art for a new device for the delivery of a fragrance to an environment such as a room or chamber wherein the fragrance is delivered in conjunction with a burning flame.

There is yet further need in the art for a fragrance delivery system which has a long and useful product service life, and which may be used to deliver a variety of different fragrances.

There is a need in the art to provide a new process for the fragrancing of a closed space such as a room, or other area, which process includes the use of a oil lamp as a heat source in a fragrance delivery apparatus.

These and other objects of the invention are satisfied by a fragrance delivery system according to the invention which is a device which includes a fluid reservoir, a wick, and a fragrance emanator located in the near proximity to that end of the wick which provides the flame. Optionally, and desirably in many instances the device includes a wick holder tube for holding the end of the wick intended to be burned in the near proximity of the fragrance emanator. This device is sometimes also referred to herein simply as a fragrance device.

DETAILED DESCRIPTION OF THE INVENTION

Figure 1:
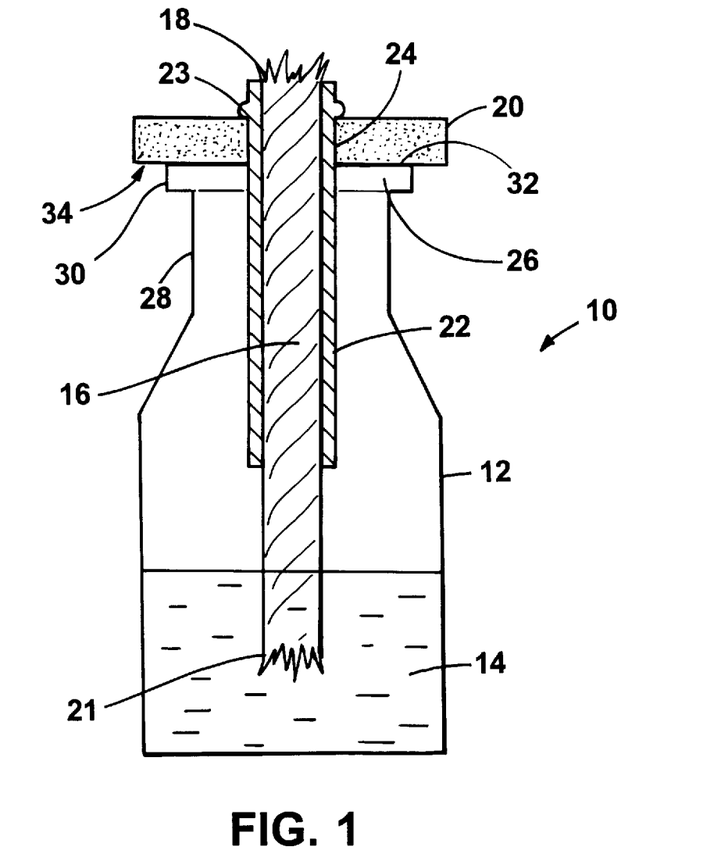
FIG. 1 illustrates the general inventive concept of the fragrance device according to the present invention.

Turning now in detail to FIG. 1 there is illustrated in cross sectional view an exemplary fragrance device 10 according to the present invention. The fragrance device includes a fluid vessel 12 which is adapted for containing a quantity of a fuel 14, a wick 16 having one end 18 extending from the interior of the fluid vessel 12 which is intended to be ignited and burned, and a second end 21 which is at least partially in contact with the fuel. The fragrance device further include an emanator element 20 located near the end 18 of the wick intended to be burned and in this exemplary embodiment, an (optional) wick holder tube 22 encasing at least part of the wick is also illustrated. As may be seen in FIG. 1, according to this embodiment the emanator element 20 includes a passage 24 therethrough which is suitably dimensioned for retaining the wick holder tube 22; the wick holder tube in turn is dimensioned to be fitted within the emanator element 20 and at the same time to encase at least a portion of the wick 16. To facilitate such a construction, the wick holder tube 22 includes a peripheral ring portion 23 which has a diameter greater than that of the passage 24 and when inserted into said passage 24, the peripheral ring portion 23 contacts the emanator element 20 and stops the further insertion of the wick holder tube 22. In an alternative, while not shown, it is to be appreciated that the peripheral ring portion 23 may be dispensed with, in which case the wick holder tube 22 may be friction fitted into the emanator element 20. In a still further alternative, the presence of such a peripheral ring 23 may be obviated wherein a part of the wick holder tube 22 is wider than the diameter of the passage 24, such as when such a wick holder tube is flared at one portion thereof, in which case the flared portion of the wick holder tube stops the further insertion of the wick holder tube 22 into the emanator element 20. The wick holder tube 22 may also be dimensioned to have a portion thereof which has a reduced external diameter which said portion may be used in conjunction with a further element, such as a clip which may be affixed to the wick holder tube 22. The thus fastened clip (or other element) has a dimension larger than that of the passage 24 and when the wick holder tube 22 is inserted into the emanator element 20 stops the further insertion of the wick holder tube 22 into the emanator element 20 at the region of the fastened clip.

Also, while not shown it further to be understood that the length of the wick holder tube may vary, i.e., it may be shortened or lengthened relative to the relative dimensions of the fluid vessel, and/or the emanator element and it is contemplated by the inventor that a portion of the wick holder tube may extend sufficiently so to be in contact with or to be immersed partially within the fuel contained within the fluid vessel.

With attention now to the relationship of the emanator element 20 and the fluid vessel 12 as illustrated in FIG. 1, the fluid vessel includes an end opening 26 at an end of a neck region 28 which is surrounded by a neck end 30. As is illustrated in FIG. 1 the emanator element 20 rests in physical contact against the peripheral margin 30. As may be seen the neck end 30 defines a generally horizontal top face 32 which is in physical contact with a flat face 34 of the emanator element 20. It is to be noted that these contacting surfaces 32, 34 are not necessarily fluid tight nor vapor tight and the emanator element 20 remains freely movable, i.e., rotatable, with respect to the fluid vessel 12.

Figure 2:
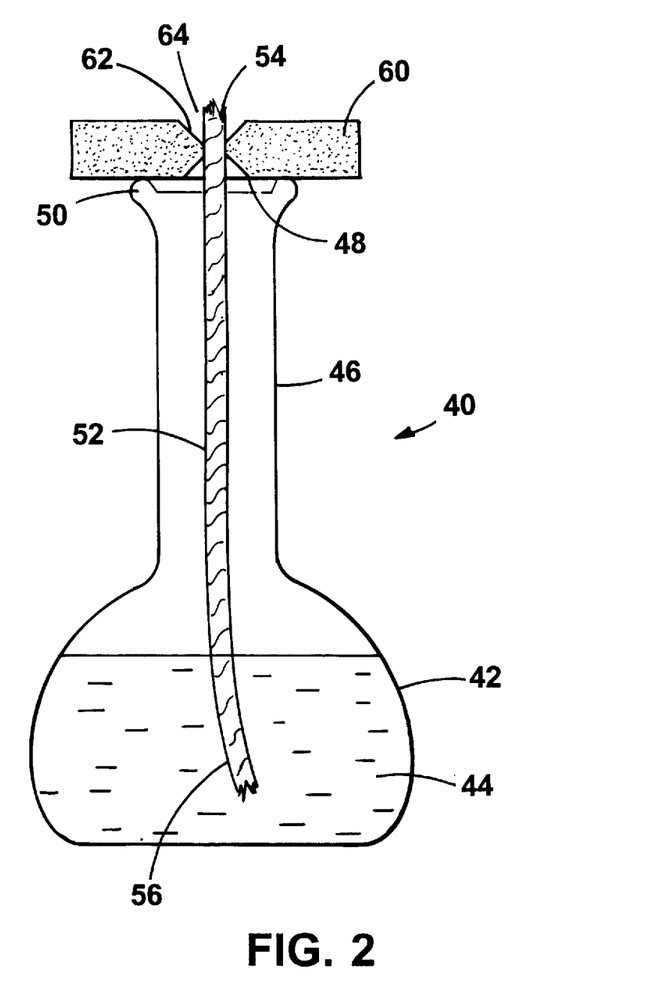
FIG. 2 illustrates a further embodiment of a fragrance device according to the present invention, without a wick holder tube.

Turning now to FIG. 2 there is illustrated in a cross sectional view a further embodiment of a fragrance device 40 according to the present invention. This fragrance device similarly includes a fluid vessel 42 containing therein a quantity of a fuel 44. The fluid vessel includes a neck region 46 which terminates at an fluid opening 48 which is surrounded by a peripheral margin 50. Further included as part of the fragrance device is a wick 52 having two ends, a first end 54 intended to be ignited by a flame and a second end 56 which is adapted to be in contact with or to be partially immersed within the fuel 44 contained within the fluid vessel 42. Further, the fragrance device includes a emanator element 60 which includes a passage 62 passing therethrough which passage includes a section having a restricted diameter 64 which is appropriately sized for physically retaining a portion of the wick 52 near its burning end 54. This passage 62 and the section having a restricted diameter 64 are formed of or faced with a non-porous surface, which denies the absorbance of the fuel in the wick to pass into the emanator element. Such may be accomplished simply by glazing the interior portion of the passage 62 and the restricted diameter 64, or by the use of a further element such as a metallic foil collar or metal ferrule or bushing which may be fitted into the emanator element. The fragrance device 40 according to FIG. 2 is to be observed to differ from the fragrance device 10 of FIG. 1 in that a relatively narrower wick is provided, a different shape of the vessel is provided, as well as the absence of a wick holder tube for the retention of the wick. In the embodiment shown on FIG. 2, the wick retention function i.e. holding it in a position relative to the emanator element 60, is provided by the construction of the emanator element itself which as is shown includes a restricted passage for mechanically retaining the wick.

With regard to the various elements of the delivery devices according to the present invention, it is to be noted first that the fluid vessel may be of any shape, form or configuration which is suited to the containment of the fuel which is to be provided therein. That is to say, it is to be clearly understood that dimensions, internal fluid volumes, shapes, and to a great degree even the materials for the construction for the fluid vessel are left to the selection by a designer. Apart from the necessity of retaining the fuel without the undesired degradation of its material of construction, various modifications to the forms of fluid vessels illustrated on the figures, and/or the specification of various fluid vessels not necessarily illustrated herein are possible and are considered to be within the scope of the present invention. Thus, various shapes and configurations of the fluid vessel based on aesthetic reasons having pleasing forms and shapes may be produced. The fluid vessel may also be used in conjunction with a further mechanical element, such as a hanger arrangement, pedestal or base. With regard to the materials of construction, just to be understood and as would be appreciated by a skilled practitioner, that the primary consideration judging the selection of such material is that as it contains a quantity of the fuel, it is not undesirably degraded by the fuel which it is to contain. Many materials which satisfy this requirement are available to the art and may be used, and it is generally preferred that low cost materials which are inflammable, and yet which may be shaped into a wide variety of forms may be used in producing the fluid vessels, by way of example these include for example glass, ceramics especially glazed ceramics, non-porous terra cotta and clays especially when fired or glazed, crystal, metal, as well as one or more materials based on naturally occurring or synthetically produced polymeric materials and such as any variety of known polymers which do not undesirably degrade (i.e., are dissolved or undesirably softened) when containing the fuel. Of these, polymers, glass, and ceramics, including glazed ceramics, are preferred due to their widespread availability at low cost, ready formability into a wide variety of useful and attractive shapes, as well as their low flammability.

With regard to the wick which is included in the delivery devices according to the present invention, the wick may be formed of known materials especially those which are known to be useful in prior art oil lamps. These include by way of non-limiting example one or more fibers based on one or more naturally occurring fibrous materials, and/or as well as one or more synthetically produced materials. Preferably, the wick is formed of a material which is only slowly consumed when ignited and used in the delivery devices according to the present invention, and of these particularly useful are non-woven glass fiber, asbestos, glass filled polymer fibers, cotton, linen, silk as well as other naturally occurring such as cotton, linen, jute, hemp or silk and/or synthetically produced fibrous materials. The diameter of the wick, as well as its shape may vary, i.e., the wick may be flat such as of a ribbon shape, as well as be hollow, or circular in cross-section. These, and other wicks of like or different cross-sectional geometries may be utilized without any detrimental effect to the present invention. Further, as is known to the art these wicks may be formed of fibers having different colors, and these too may be utilized and in some cases are to be preferred in providing an aesthetically pleasing effect to the overall delivery device according to the invention.

Fragrance materials which find use in conjunction with the present invention include generally, all liquids which are at least in part volatilized when heated, particularly those which are volatilized when heated to a temperature in excess of room temperature (approx. 68° F., 20° C.) and most preferably those which are volatilized at or below flame temperature of the burning wick of the delivery device. Such fragrance materials particularly include those which emanate a fragrance or scent when volatilized, and are generally scented oils or perfumes which may be a pure essence oil or which may be a mixture of constituents such as a minor amount of a perfume or pure essence oil diluted in a greater volume of a volatile liquid base such as an alcohol or other hydrocarbon. Many such materials are known to the art, and although not specifically described here, may be used and are considered within the scope of the present invention.

It is also contemplated that in the place of, or in conjunction with one or more of the fragrance materials described above, other volatile liquids particularly include insect repellent compositions, deodorizing compositions, medicinal compounds, herbal compositions as well as disinfectant compositions may also be used.

The fuel which may be used with the delivery devices according to the invention may be any which is found suitable to ensure the operation of the delivery device in the manner being described herein. Many useful fuels are based on organic compounds, especially lighter distillation fractions of petroleum. Such fuel includes for example, alcohols, kerosene and lower hydrocarbons as well as mixtures of two or more such materials. The fuels themselves may include a coloring agent such as a soluble dye or other coloring agent which improves the attractive appearance of the fuel, and may improve the mood enhancing characteristics of the fragrance delivery systems according to the invention. Such a fuel may further include one or more flame coloring materials such as metal salts including copper, sodium and others which when burned vary the color of the flame to a color other than that of the burning fuel without such flame coloring materials.

The fragrance devices according to the invention include a emanator element which desirably includes at least one passage passing therethrough which is adapted to permitting the retention and/or passage of at least a portion of the wick, with or without the wick holder tube. This emanator element may be formed of or include a porous ceramic material. Such useful ceramic materials are any of a large class of nonmetallic, inorganic materials containing high proportions (i.e., at least 75% wt.) of silicon, silicon oxide, silicates as well as other materials not particularly elucidated here, and which have a porous structure which acts to absorb or entrain the fragrance material. These include clays, porcelains, terra cotta, talc, cements as well as other ceramic materials which are known to the art which feature a porous structure.

The emanator element may also be formed of or include a porous non-ceramic material as well. Such may be any of a variety of materials which by way of example includes paper, paper mache, fibrous substrates whether made of naturally occurring or synthetically produced fibers including blends of two or more of these classes of fiber, woven and non-woven textile materials, compressed fibrous structures including felt and felt like materials, foams especially foamed polymeric materials and sintered polymeric materials. By way of example and not by way of limitation, exemplary polymer materials which may be used to form the emanator element in accordance with the present invention include polyolefins such as polyethylene, polypropylene, polybutylene. Copolymers and physical blends of two or more different polymers may also be used in the construction of the emanator element as described in this specification. Polyolefins are generally preferred due to their relatively widespread availability, low cost, and ease of fabrication. These preferred polyolefin polymers may be of any molecular weight, and degree of linearity or branching, and which exhibit appropriate physical properties. Particularly useful polyolefins include polyethylene and polypropylene which may be formed into porous, foam like constructions. Such a polymeric emanator element according to the invention may be produced by providing the selected polymer in the form of comminuted particles such as beads, pellets, powders, as well as other small particulate forms to the interior of a die, which die has a cavity of a configuration which matches that of the desired emanator element examples of which include any one of the embodiments described above as well as others which fall within the scope of the present invention.

It is required only that such an emanator element be heat-tolerant such that it may be used satisfactorily used in the manner described herein and that it be porous in nature. Where the emanator element is formed of a ceramic material as described above, such provides the advantage of being inflammable. Where the emanator element is a porous polymeric material also as described above, such are generally considered to be unbreakable. The emanator element is a porous material and contains intertices or internal voids which act to releasably absorb the fragrance material. Either may be used while the emanator element is desirably a single unit element as is described herein and illustrated in the accompanying figures, it may also be formed from a plurality of unit elements.

The emanator element according to the present invention is suited to retain a quantity of a fragrance material which may be introduced thereinto by any available means, such as by soaking or at immersing the same in a volume of the fragrance material, as well as by pouring or spraying the fragrance material onto one or more surfaces of the emanator element. In any of these cases, the fragrance material is permitted to be entrained within the emanator element and most desirably the emanator element is nearly or completely saturated with the fragrance material.

During operation of the fragrance device, the emanator element is positioned in sufficient proximity to the burning end of the wick such that a part of the heat generated by the flame is transferred to the emanator element. Such a transfer of heat may be by radiation transfer and/or by conductive transfer from the wick and/or wick holder tube to the emanator element. In this manner, sufficient heat from the flame is imparted to the emanator element such that at least a part of the emanator element is heated sufficiently to volatilize an amount of the fragrance material. In this way, the fragrance material is volatilized and delivered to the surrounding environment. An advantage of such a fragrance delivery operation flowing from the use of the fragrance devices according to the invention is that the fragrance material most proximate to the burning flame is delivered to the surrounding environment first but is naturally replenished from other portions of the emanator element more distantly located from the burning flame. In this manner, a relatively constant output of fragrance by the delivery device during the operating life of the emanator element is provided. Consequently a controllable and uniformed fragrance delivery pattern may be achieved.

With regard to the emanator element, a further feature which is provided by the delivery device of the present invention is that such a delivery device may be utilized several times, even indefinitely, whereby when the fuel is consumed within the fluid vessel, it may be replenished by merely providing more fuel into the interior of the fluid vessel. Similarly, when the emanator element approaches the end of its service life, i.e. the time at which all, or substantially all of its fragrance has been evaporated, it may be removed and discarded and a new emanator element may be installed in the fragrance device. However, it is also contemplated that the emanator element may be replenished by providing it with a further quantity of a fragrance material and once replenished, it may be reused by replacing it in the delivery device. The emanator element may be replenished by removing it from the fragrance device and immersing it or dosing it (spraying, pouring, brushing on) with a further quantity of a fragrance material, but it may also be replenished without removing it from the delivery device if so desired. It is also to be understood that different fragrances may be utilized with one emanator element, namely when an emanator element approaches the end of its useful product life, it may be replenished with a fragrance different than with which it had been used previously.

Thus, a fragrance device useful for providing different fragrances during the useful product life of the overall delivery device is now possible. Such devices are believed to have been hitherto unknown.

A further advantageous feature of the fragrance devices according to the invention is that it is contemplated that emanator elements may also be interchanged in the fragrance devices during the course of their useful product life, namely prior to the exhaustion of the fragrance material which they contain. In such a manner, a consumer of the fragrance device may have a selected fragrance "at will", with no need to have an installed emanator element be used until its fragrance material is totally consumed before removing it and replacing it with a further emanator element.

A still further advantageous feature of the fragrance devices according to the invention is that as the devices may serve to deliver not only different fragrances "at will" as described above. Namely, as such different volatile substances which may be delivered by the fragrance delivery device according described herein may be used to deliver insect repellent compositions, deodorizing compositions, medicinal compounds, herbal compositions as well as disinfectant compositions, it is contemplated that the fragrance delivery device of the invention may be interchangeably used to deliver such a different volatile substance which may have an unpleasant or undesired scent, and after such a material is delivered, the emanator element containing such different volatile substance is removed from the delivery device and is substituted by a fragrance containing emanator element which may be used to mask or neutralize the scent of the previously used material. Such a method of use of alternating between a fragrance material and a different volatile substance such as a insect repellent composition, deodorizing composition, medicinal compound, herbal composition, or disinfectant composition which may have an unpleasant or undesired scent associated with their volatilization provides a method for effective treatment of an environment such as a closed room without an undesirably long duration of an undesirable or unpleasant scent. Further, such a method of use of alternating between a fragrance material and a different volatile substance in the fragrance delivery devices according to the invention provides for a method for systematic and regular treatment of an ambient environment, such as in a closed room wherein a different volatile substance as denoted above may be volatilized and delivered to an ambient environment for a first time interval, and fragrance material may be then delivered to the ambient environment for a second time interval which acts to mask or neutralize any unpleasant odors of the insect repellent composition, deodorizing composition, medicinal compound, herbal composition, or disinfectant composition previously delivered. Such a method may be regularly repeated, in which manner a constant and effective level of an insect repellent composition, deodorizing composition, medicinal compound, herbal composition, or disinfectant composition may be maintained in an ambient environment without an undesirable odor being also present, said odor having been masked or neutralized by the subsequent or prior delivery of the fragrance material.

A further advantageous embodiment of an emanator embodiment according to the invention is one wherein two or more different fragrance materials may be delivered simultaneously. This is accomplished by providing a plurality of emanating elements which are used simultaneously. According to one embodiment, this is simply accomplished by providing two or more separate emanating elements to the fragrance delivery devices in the proximity of the wick wherein during the burning of the wick's end, sufficient heat is generated to volatilize a portion of the fragrance material from each of the emanator elements. For example, this may be accomplished by stacking in register two or more emanator elements. In the alterative, there may be provided two or more emanator elements which are fittable together, i.e., such as semi-circular elements, wedge-shaped emanator elements which may be fitted together to form an emanator element according to the invention.

The further particular advantage of such an embodiment is that a great degree of flexibility is afforded to the consumer of the fragrance delivery devices according to the invention. For example, it is possible to have "custom" fragrances wherein the consumer may provide two or more emanator elements having different fragrancing materials entrained within to a fragrance-delivery device, and as both are simultaneously heated and their fragrance materials are volatilized, unique and pleasant fragrance combinations may be provided. Similarly, as it is understood that the fragrancing material may be other materials such as insect repellent compositions, deodorizing compositions, medicinal compounds, herbal compositions, or disinfectant compositions, it is also possible to simultaneously deliver, for example, both a fragrancing material as well as one or more of the other compositions described above, this is particularly advantageous for example wherein an unpleasant or undesired scent may be associated with a certain composition which may be then deodorized, masked, by the use of another of the fragrancing materials.

A further advantage of such a plural emanating elements is also wherein it is desired to have a higher delivery rate of the fragrance material to an ambient environment during a certain timed interval. This may be therefore simply accomplished by providing the two or more emanator elements containing a quantity of fragrance material (or other materials recited above) within to a delivery device according to the invention. As the individual emanator elements are simultaneously heated, a greater rate of volatilization of the fragrance materials (or other composition) may be achieved in a unit length of time and therefore providing a greater fragrancing or other treatment effect to an ambient environment such as the interior of a room.

In accordance with a further particular embodiments of the invention, plurality of comminuted emanator elements are provided, the said emanator elements are in the form of small comminuted particles, such as in the shape of small beads, pellets, and the like which are individually provided with a fragrance material or other material recited above. Such may be made of the ceramic or non-ceramic materials as described above, especially ceramic and porous polymer materials.

Such comminuted emanator elements may then be used in various combinations, i.e., a quantity of comminuted emanator elements containing a first fragrance material may be combined with a quantity of further comminuted emanator elements containing a second fragrancing material. Such a combination then permits for the consumer to produce "custom fragrances" such as by varying the selection of the two or more fragrancing materials used, as well as the individual proportions of the comminuted emanator elements containing each of the said plural fragrance materials. Similarly, there may be used comminuted emanator elements having entrained within one or more of the other materials such as insect repellent compositions, deodorizing compositions, medicinal compounds, herbal compositions or disinfectant compositions which may be similarly mixed with comminuted emanator element containing one or more fragrancing compositions. As will be understood, the use of such comminuted emanator elements in conjunction with a fragrance delivery device according to the invention, provides for a great degree of flexibility in the delivery of volatile materials to an ambient environment, such as the interior of a room or other closed space.

While it is to be clearly understood that the primary fragrancing benefit of the delivery device according to the invention is that provided by the emanator element, it is further to be understood that as a supplement and/or adjuvant a degree of fragrancing may be provided by including a fragrance or other volatilizable material as a portion of or as the fuel within the fluid vessel. It is to be understood however that the benefits of such a material within the fuel oil is generally of little or no fragrancing benefit. As has been discussed previously, such fragrancing oil is generally consumed by the flame resulting in little or no fragrance delivery to the environment, and it has been observed that only a small fraction of the fragrance or other volatilizable material which is incorporated as a portion of the fuel provides any fragrancing effect to the ambient atmosphere.

A further benefit of the emanator element according to the invention is that due to its porous nature, in conjunction with the volatile characteristics of fragrance materials, is to be understood that even when the delivery device is not ignited that nonetheless a small, but in many cases appreciable fragrancing effect is provided to the environment. This is due to the fact that the surface area of the emanator element in contact with the surrounding air provides an effective vapor transfer surface for the fragrance material which permits a fragrance may slowly evaporate into the surrounding air. This rate of course is much lower than that at which it would evaporate when the delivery device is ignited.

Figure 3A:
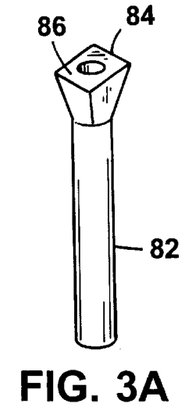
FIGS. 3A, 3B, 3C and 3D illustrate alternative embodiments by way of illustration of wick holder tubes.
Figure 3B:
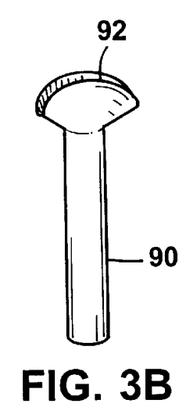
Figure 3C:
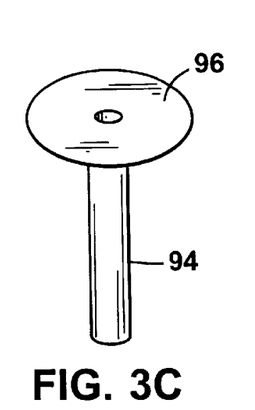

The emanator element according to the invention may take a variety of shapes and forms and are generally required that it be formed of the nonflammable porous material, preferably one or more of the materials described above and that it include a passage adapted to permit the passage of the wick therethrough. Such a passage may be as that shown on FIG. 1 wherein substantially straight sides are in a close-fitting relationship to the wick holder tube or in the alternative, where a wick holder tube is not present, it may be desired to dimension the passage such to include a restricted portion having a smaller cross-sectional area than other parts of the passage wherein the wick may be physically retained during the operation of the delivery device. Such a construction is shown on FIG. 2. optionally but desirably, the delivery device includes a wick holder tube having a cross section adapted to conform to the cross section of the wick, which for example may be a circle. The wick holder tube encases at least a part of the wick, and physically retain the same therein. Any of a variety of constructions is possible and in certain embodiments, as is illustrated on FIGS. 3A, 3B, and 3C, one of the ends is shaped to have a cross-sectional area other than that of the remaining parts of the wick holder tube. With regard to FIG. 3A there is illustrated a generally circular wick holder tube 82 having a shaped end 84 which is described as being a flared shape terminating in a rectangular end portion 86. In FIG. 3B is illustrated a further embodiment of a wick holder tube 90 having for the most part a generally uniform circular cross-section which terminates at one end in a flattened flared lightly opened clam-shell shape 92, and as is shown on FIG. 3C. Also illustrated is a yet further embodiment of a wick holder tube 94 which terminates at one end thereof in a flat, generally circular disk-shaped end which extends substantially perpendicularly to the remaining portions of the wick holder tube 94. The function of such shaped ends is in some degree to control or to influence the pattern of the burning flame at the end of the wick inserted within the interiors of such wick holder tubes. In some cases the pattern of the shaped ends of the wick holder tubes may influence the heat distribution of the flame and thereby the overall fragrance delivery characteristics of the delivery device. Specifically with reference to the wick holder tube according to FIG. 3C, the flared circular end 96 when inserted through the passage of an emanator element (such as that illustrated on FIG. 1), will be understood that the disk portion 96 will be in interfacial contact with a surface of the emanator element. When the wick is ignited, the heat from the flame could be expected to radiate at least across the disk portion 96 and to be thereby more evenly distributed across the surface of the emanator element 20 of FIG. 1.

Figure 3D:
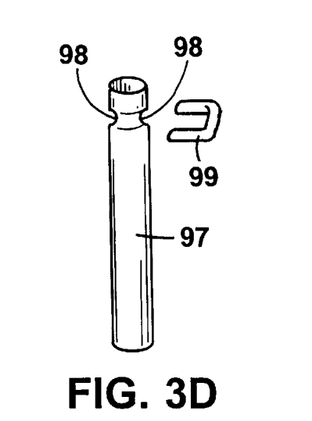

Illustrated on FIG. 3D is a wick holder tube 97 having a portion of reduced diameter which is at the region of two recesses 98. The recesses 98 function on the interior of the wick holder tube 97 to retain the wick (not shown) therebetween, and simultaneously, are adapted to receive a clip 99 within. The clip 99, when inserted has a dimension greater than the diameter of the passage of an emanator element and thus, when the wick holder tube 97 is inserted into such passage, the further insertion of the said tube 97 is stopped as the clip 99 contacts the emanator element.

Figure 4A:
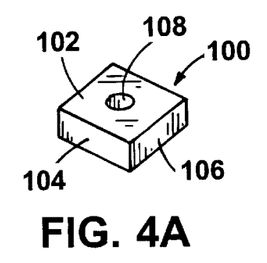
FIG. 4A, 4B, 4C, 4D, 4E, 4F, 4G, 4H, 4I, 4J and 4K illustrate emanator elements according to the invention in various alternative embodiments.

Various embodiments of emanator elements are illustrated in the perspective views of FIGS. 4A, 4B, 4C, 4D, 4E, 4F 4G, 4H, 4I, 4J and 4K. Turning now particularly to FIG. 4A, therein is shown a perspective view of an emanator element 100 which has a essentially square face 102 and rectangular sides 104, 106 and further includes a passage therethrough 108. The relative dimensions of the faces, sides, and the passage therethrough will be understood to be variable with the ultimately desired dimension of the delivery device according to the invention.

Figure 4B:
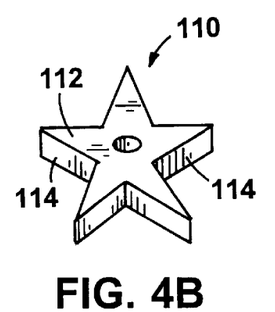

Turning now to FIG. 4B there is shown a perspective view of an emanator element 110 in the form of a 5 pointed star which includes a star-shaped top face 112 and a plurality of side faces 114 corresponding to the thickness or height of the emanator element.

Figure 4C:
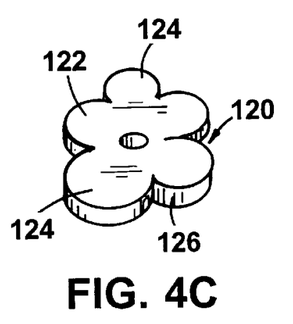

Turning now to FIG. 4C therein is shown a yet further embodiment of an emanator element 120 according to the invention, herein in the shape of a flower having a top face 122 having a plurality of lobes 124 representative of flower petals, as well as a series of curved faces 126 corresponding to thickness or height of the emanator element 120.

Figure 4D:
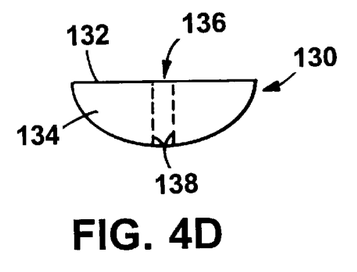

Turning now to FIG. 4D therein is shown a cross-sectional view of a still further emanator element according to the present invention 130 which is in the shape of a flattened hemisphere having a top surface 132 and a curved continuous bottom surface 134 which is generally described as hemispherical in form. Also illustrated on the Figure by the dotted lines is the passage 136 which may be seen as generally straight walls 138 and it is to be further understood that this central passage is generally cross circular in form.

Figure 4E:
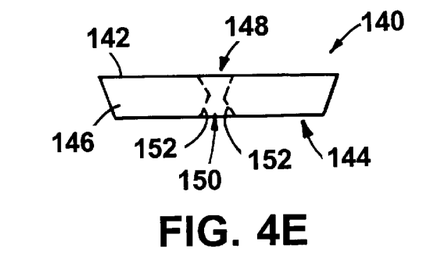

Turning now to FIG. 4E there is illustrated a yet further embodiment of an emanator element 140 according to the present invention which includes a top face 142, a bottom face 144, a continuous side 146. This emanator element may be described to be frustro-conical in its general geometric shape, and further includes a central passage 148 which includes a restricted passage 150 at approximately the mid-point of the distance between the top face 142 and the bottom face 144. This restricted passage is formed by a diminishment in the cross-sectional dimension between the side walls 152 of the central passage 148 at a point, here shown to be approximately mid-way, between the top face 142 and the bottom face 144. It is to be understood however that such a restriction may be located at a different position relative to one or more of the faces of the emanator element 140.

Figure 4F:
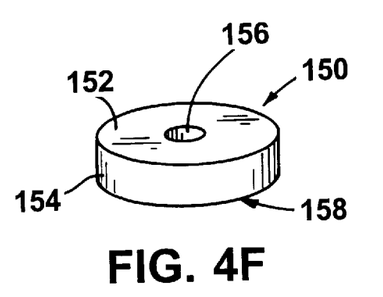

Various modifications of the general construction of the emanator element as has been described generally above are also possible and are to be understood to be within the scope of the invention. One such modification as is illustrated on FIG. 4F is the inclusion of a peripheral film or foil. Turning now to FIG. 4F there is illustrated a perspective view and emanator element 150 having a top face 152, a side face corresponding to the thickness 154 and a central passage passing therethrough 156. While not shown, it is to be understood that a bottom face 158 similar to the top face is also present, and further that this embodiment may be readily substituted for the emanator element 20 as illustrated on FIG. 1, as well as being substituted for the emanator element 60 of FIG. 2. With specific to the perspective view offered by FIG. 4F, therein is illustrated a metal foil which faces the side face 154 of the emanator element 150. The inclusion of such a foil provides several specific benefits to the emanator element. First, such metallic foil limits the vapor transfer effective area of the emanator element according to the invention and thereby in some regards diminishes the delivery rate of the fragrance from the emanator element particularly when the delivery device is not ignited. Second, the presence of the foil about the side wall 154 of the emanator element 150 may provide the benefit of a more uniform heat radiation and/or heat conduction of the emanator element when the delivery device is ignited. In this way, a constant fragrance delivery characteristic may be provided and/or insured. A further benefit attendant upon the use of the foil facing is that a variety of printed foils, and/or colored foils may be used thereby enhancing the overall attractive appearance of the emanator elements when provided, which further may improve the consumer appeal of such a product, of course in addition to the prior technical benefits denoted above.

Also, while it is not illustrated on FIG. 4F it is to be further understood that further portions, specifically the bottom face 158 as well as the top face 152 of the emanator element may in whole or in part be faced with such a metal foil. Facing such bottom face with a metal foil will also be expected to improve the vapor delivery characteristics of the delivery device in limiting the vapor transfer effective area of the emanator element 150. It is contemplated as well as the foil for encasing part of the surface of the emanator element may be any variety of known metal, metallic foils and or films which include metal foils, as well as certain heat resistant polymer films which may be embedded with metallic particles and which are shown to be sufficiently heat tolerant to the operating characteristics of the delivery device.

The inclusion of such a facing material useful in encasing at least a portion of the emanator element also permits for the use of the non-ceramic porous materials described above, especially the porous polymeric materials and the fibrous materials to be used in the fragrance delivery device being described herein. The use of such a foil or film as described in forming an emanator element provides for a reduced risk of flammability and/or melting of the porous material which is used in entraining the fragrance material. Further where the emanator element is a foil or film which is of sufficient stiffness it may be used to produce a self-supporting rigid casing element useful in conjunction with the porous element in producing the emanator element according to the invention.

Encasing the emanator element also permits for a degree of control in the delivery of the fragrance material. For example, encasing an emanator element and providing only a number of holes or other passages greatly shows the volatilization and release of fragrance material into a room.

Figure 4G:
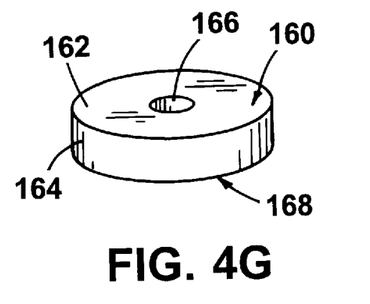

Turning now to FIG. 4G there is illustrated a further embodiment of an emanator element 160 according to the present invention. Such an emanator element similarly includes a top face 162, a side wall 164 which is essentially circular in nature and which corresponds to the height or thickness of the emanator element 160, a central passage 166 adapted for permitting the passage for at least a portion of the wick therethrough and, although not shown a bottom face 168 parallel to and corresponding to the top face 162. Unlike the foil or film which is shown to encase a portion of the emanator element 150 according to FIG. 4F, on the present FIG. 4G, a portion of the surface of the emanator element 160 is glazed in accordance with any variety of ceramic glazing materials, using known materials which may be applied by known techniques. The use of such a glaze provides a further alternative means by which the effective vapor transfer surface area of the emanator element may be limited thereby limiting the loss of the fragrance material from the interior of the emanator element, while at the same time is provided an attractive appearance to the emanator element forming part of the delivery device. As will be appreciated by one skilled in the art, the glazing may be produced in a variety of shades, sheens, and/or colors which may be similar to or distinctly different from that of the material used to form the emanator element. Further, striations, patterns, and other visual characteristics may be imparted by the use of such a glazed surface. Further, such a glaze material is essentially incombustible and is also readily produced at low cost.

It is to be clearly understood that the use of a film foil as described in conjunction with FIG. 4F or the use of a glazed surface for part of the surface of the emanator element 160 as described in FIG. 4G may be used in conjunction with any other emanator element of a different geometry such as any of those illustrated on FIG. 4A–4E and described previously, as well as FIG. 4G discussed below.

Figure 4H:
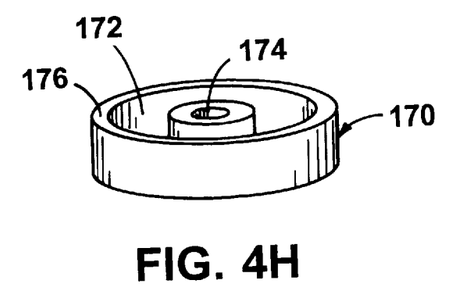

With regard now to the emanator element illustrated on FIG. 4H, therein is illustrated a perspective view of an emanator element 170 which in cross section includes an annular recess or trough 172 which is of a generally "U" shaped cross section, as well as a passage 174 passing through the emanator element 170.

In use, the trough is filled to a point coincident with the top surface 176 of the emanator element 170 with a fragrance material, which is then permitted to seep into the interior pore volumes, i.e., the pores of the emanator element. Desirably, the volume of this trough is so dimensioned that its volume is less than or equal to the total pore volume of the porous ceramic material of which the emanator element is constructed. Such an emanator element having such a relationship between the total volume of the trough and the total pore volume of the emanator element is one which is difficult to overfill with a fragrance material and is thus advantageously used when the emanator element is to be replenished without disassembly or removal from the delivery device. Such is advantageous when refilling is to be done by the consumer of the fragrance delivery device.

Figure 4I:
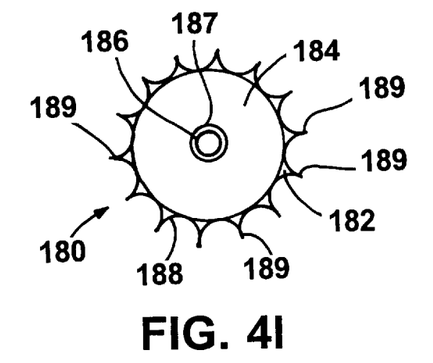

With regard now to FIG. 4I therein is illustrated a top view of a further embodiment of an emanator element 180 according to the invention which comprises a casing element 182 formed of a self-supporting rigid metal foil or film containing metallic particles, and a porous element 184 formed of a ceramic or non-ceramic porous material which contains a quantity of a fragrance material entrained within. The porous element 184 has a passage 186 passing therethrough which is dimensioned to receive a center post portion 187 of the casing element 182, and is further dimensioned to be fittable within the outer wall 188 of the casing element 182. While not shown, it is to be understood that the casing element 182 includes a bottom between the outer wall 188 and the post portion 187 and thus defines a trough or generally "U" shaped cross section. The outer wall 188 as illustrated includes a plurality of flutes 189 which function as radiator ribs and provide extra cooling to the region of the porous element 184 distal to the passage 186. Also, as may be seen from the figure, the diameter of the passage 186 is larger than that of the center post portion 187 of the casing element 182 and in this way direct physical contact between the center post portion 187 and the porous element 182 may be avoided. Such may be advantageous wherein the porous element 182 is formed of a non-ceramic material especially a porous polymeric material as described above. Thus, it will be understood that the porous element 184 may be loosely fitting within the casing element 184, and both form an embodiment of the emanator element according to the invention.

Figure 4J:
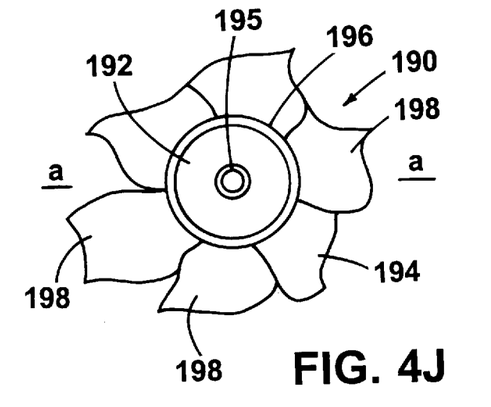

Turning now to FIG. 4J therein is illustrated in top view a further embodiment of an emanator element 190 according to the invention which includes a porous element 192 which may be formed of a ceramic or non-ceramic porous material as discussed above contained within a casing element 194. The casing element 194 includes a center post portion 195 extending upwardly from a bottom 196, a side wall portion 197 and a peripheral portion 198 extending from the side wall portion 197. As is illustrated, the center post portion 195, the bottom 196 and the side wall portion have a "U" shaped cross section and define an annular trough which is dimensioned to contain the porous element 192 within.

Figure 4K:
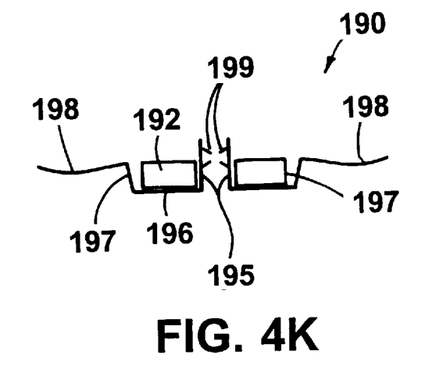

With regard to the specific embodiment of the emanator element 190 shown in FIG. 4K, casing element may be formed of a foil or metallic particle containing film, but is desirably a self-supporting rigid casing element. The peripheral part 198 is in the form of a plurality of lobes, which are leaf shaped or petal shaped as illustrated and said peripheral part 198 function as radiator ribs to provide extra cooling to the region of the porous element 192 distal to the passage 199.

Turning now to FIG. 4K there is illustrated the embodiment of the emanator element according to the FIG. 4J, wherein the same elements are correspondingly numbered. As may be seen in more particular detail the center post portion 195, the bottom 196 and the side wall portion 197 have a "U" shaped cross section which define an annular trough which is dimensioned to contain the porous element 192 within. Such a configuration regarding the "U" shaped cross section defining an annular trough is analog out to that of the configuration of the emanator element 180 illustrated on FIG. 4I. Further as may be seen from FIG. 4K, the peripheral parts 198 extend from the side wall portion 197 of the emanator element 190. Illustrated by means of dotted lines is illustrated a portion 199 of the center post portion 195 having a reduced cross section which may be dimensioned to retain a portion of the wick therebetween. It will be understood however that such a portion 199 need not be present, in which case a wick holder tube (not shown) may be readily inserted into the center post portion 195. As may be seen from the figure, the center post portion 195 has a height from the bottom 196 greater than the height of the porous element 192. Such a configuration is advantageous particularly where in the porous element 192 is formed of a non-ceramic porous material as described above. Further as may be seen, the porous element 192 is loosely fitting and does not necessarily contact the center post portion 195 which arrangement may also be desired wherein the porous element 192 is formed of a non-ceramic porous material, such as a sintered polymeric material, as described above. Such an arrangement desirably avoids the possibility of melting a porous element 192 formed of such a sintered polymeric material.

With respect to the container elements 182 (of FIG. 4I) as well as container element 194 (of FIGS. 4J, 4K) such are desirably formed by cutting, stamping, pressing crimping or other forming step or steps from a metal sheet or metal plate. Generally this is a one-step process. Afterwards the porous element (184) (192) is inserted into the annular trough of the container element. The porous element may be pre-impregnated with the fragrance material or may be impregnated with the fragrance material following its insertion into the container element.

Figure 5:
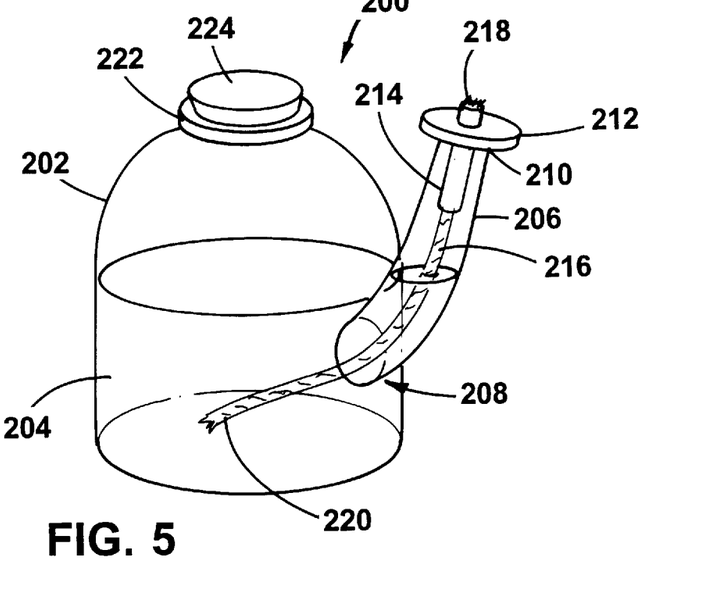
FIG. 5 illustrates a yet further alternative embodiment of a fragrance device according to the present invention, illustrating an alternative fluid reservoir design.

Turning now to FIG. 5 therein is illustrated a yet further alternative design for a delivery device according to the present invention in the form of a "teapot" design. As is shown therein there is provided a delivery device 200 which includes a fluid vessel 202 adapted for retaining an amount of a fuel 204 within, and which includes a spout portion 206 extending from a region proximate to the bottom 208 of the vessel and terminating at an open end 210. The open end 210 is provided with an emanator element 212 which rests in contact with the open end 210. The emanator element 212 further retains a wick holder tube 214 which contains therein a wick 216 having one end intended to be ignited and burned protruding 218 and a second end 220 in contact with the fuel 204 contained within the vessel.

In order to provide a suitable and simple means for refilling the vessel 202 there is also provided an opening 222 which is provided with a stopper 224. By physically removing the stopper, the vessel may be readily replenished by pouring fuel through the opening 222. Further, where the stopper 224 is loosely fitting and or is not vapor-tight, a means to easily vent the interior of the vessel to the atmosphere is provided.

Figure 6:
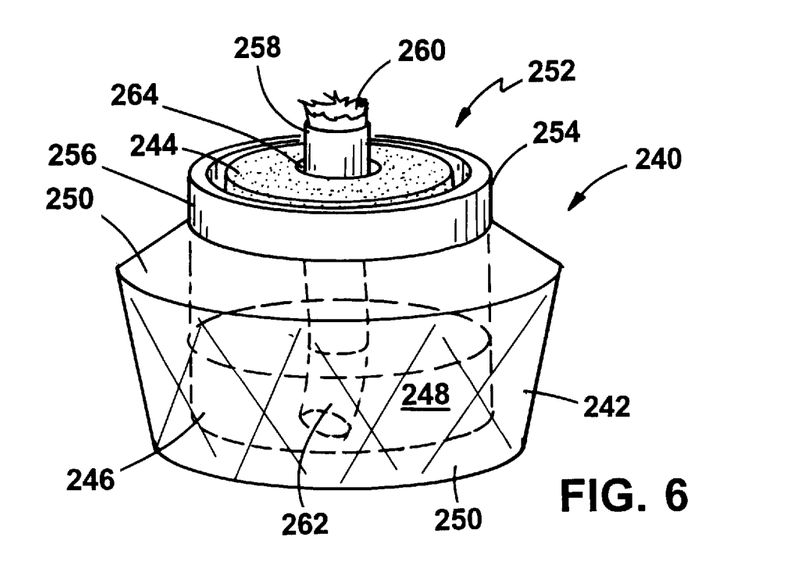
FIG. 6 illustrates a further alternative embodiment of a fragrance device according to the present invention, illustrating an alternative fluid reservoir design and an emanator element which includes a non-ceramic porous material.

FIG. 6 illustrates a further alternative embodiment of a fragrance device 240 according to the present invention, illustrating an alternative fluid reservoir 242 design and an emanator element 244 which includes a non-ceramic porous material. The fluid reservoir 242 includes an inner cavity 246 which is adapted to contain a quantity of fuel 248 therein, and a decoratively patterned exterior wall 250 surface. The inner cavity 246 terminates at an opening (not shown) which is covered by an emanator 252 which comprises an emanator element 244 contained within a casing element 254. The casing element 254 is formed from a metal sheet or plate, and is rigid and self supporting. The casing element includes a bottom (not shown) from which depends an upwardly extending exterior wall 256 which on the periphery of the casing 254, from which bottom also depends an upwardly extending center post part 258 which is at least as high as the height of the exterior wall 256. The center post part 258 functions also as a holder for a wick 260 which has one end 262 in contact with the fuel 248 contained in the cavity 246.

Annularly surrounding the center post part 258 is a porous element 244 which is formed of a porous polymeric material, and which contains a quantity of a volatile substance entrained within. As is illustrated, the porous element 244 has a passage 264 passing therethrough having a which has a diameter greater sufficiently larger than the outside diameter of the center post part 258, and the porous element 244 has an overall diameter which is sufficiently smaller than the diameter of the casing 254. As the porous element 244 does not contact the center post part 258 which retains the burning end of the wick 260, melting of the porous element 244 is diminished.

It is to be understood however, that a ceramic porous material may be used in the place of the non-ceramic porous element 244 shown in FIG. 6, and that the relative dimensions of the porous element and the container element may be varied from those described in conjunction with FIG. 6.

Figure 7:
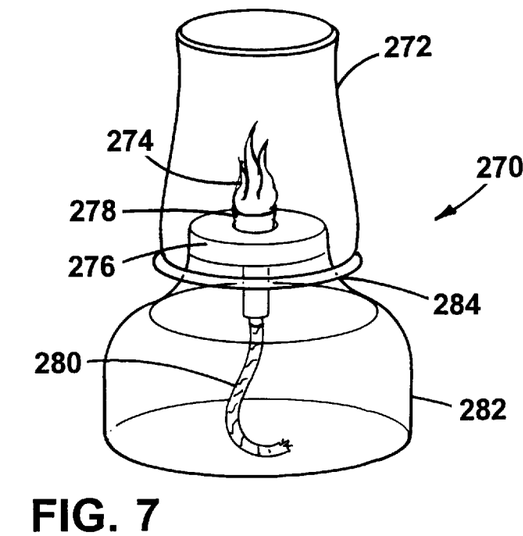
FIG. 7 illustrates an embodiment which includes a chimney.

FIG. 7 illustrates an embodiment of a fragrance delivery device according to the present invention 270 which includes a chimney 272 surrounding the end of the wick 274 which is ignited. Further shown in FIG. 7 is an emanator element 276 which circumferentially surrounds a wick holder tube 278 which retains a portion of the wick 280 within. As illustrated in FIG. 7, the chimney 272 desirably surrounds the flame when the fragrance delivery device 270 is operating which provides an enhanced degree of safety. Further, the chimney, which is desirably made of a transparent or translucent fire-retardant material, especially glass, provides a pleasing visual effect, particularly when the glass is colored. The chimney 272 may be simply placed upon the fluid vessel 282 where it is desirably retained in a generally upright position. Desirably, this point of contact at the base portion of the chimney 272 is either loosely fitting or is fitted in such a manner that a sufficient degree of air flow passes to provide ample oxygen supply to permit the continued burning of the wick 274. Alternative means for fastening the chimney 272 relative to the fluid vessel 282 are also contemplated and may include any of a variety of means known the art such as providing a more tightly friction fitting at the region of the base portion of the chimney 272, with appropriate vent means. For example, in such an embodiment the appropriate vent means may be the provision of one or more holes passing through the base portion of the chimney 272 to permit the desired air flow therethrough. An alternative, mating screw threads may be provided to a portion of the chimney 272 particularly at or near the bottom portion 284 thereof, which operate in conjunction with mating screw threads also provided on a portion of the fluid vessel 282. In this way, a better mechanical engagement between these elements is easily provided. In such case, it is also desirable to include vents to permit the flow of oxygen, again which may be provided such as by providing one or more holes at or near the base portion 284 of the chimney 272.

In a further embodiment which is not shown, but which is understood to those skilled in the art, to use of a peripheral ring, series of clips, or the like, such as are known in the application of chimneys in traditional kerosene lamps may also be utilized.

It is to be understood that the inclusion of a chimney 272 may be utilized in conjunction with any of the fragrance delivery devices according to the invention as being taught herein.

Figure 8:
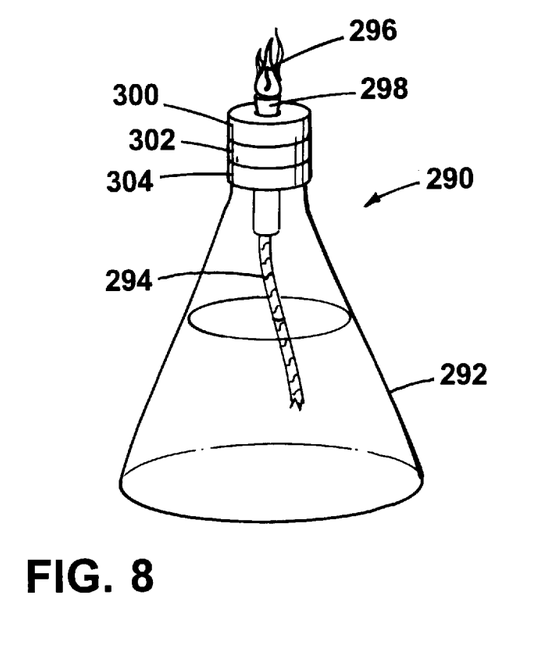
FIGS. 8 and 9 illustrate embodiments with plural emanator elements.

Turning now to FIG. 8, therein is illustrated an embodiment of the fragrance delivery device wherein plural emanator elements are provided. As is illustrated, the fragrance delivery device 290 includes a fluid vessel 292, a wick 294 having one end intended to be burned 296 as well as a wick holder tube 298. In accordance with the embodiment illustrated, a plurality of emanator elements here, three individual emanator elements 300, 302, 304 are illustrated contacted with one another and in a stacked relationship with the wick holder tube 298 passing therethrough. As has been denoted in the specification, it is to be understood that a plurality of different fragrance materials may be individually provided to each of the several emanator elements 300, 302, 304 illustrated therein. In such a manner, the ultimate consumer of the fragrance delivery device may produce a "custom" fragrance by combining two or more different fragrance materials. In a further alternative, which is also illustrated in FIG. 8, each of the individual emanator elements 300, 302, 304 may contain the same fragrance material, in which case an enhanced delivery rate to an ambient environment such as the interior of a room over a unit period of time is possible, as compared with the use of only one of the fragrance emanators as illustrated. In a further embodiment, also as is depicted in FIG. 8, it is to be understood that one or more of the emanator elements may include a volatile material other than the fragrance material such as, for example, insect repellent compositions, deodorizing compositions, medicinal compositions, disinfectant compositions and/or herbal compositions. In such a manner, they may be simultaneously delivered in conjunction with a different volatile material, especially a fragrance material which may be useful in masking their order when volatilized.

Figure 9:
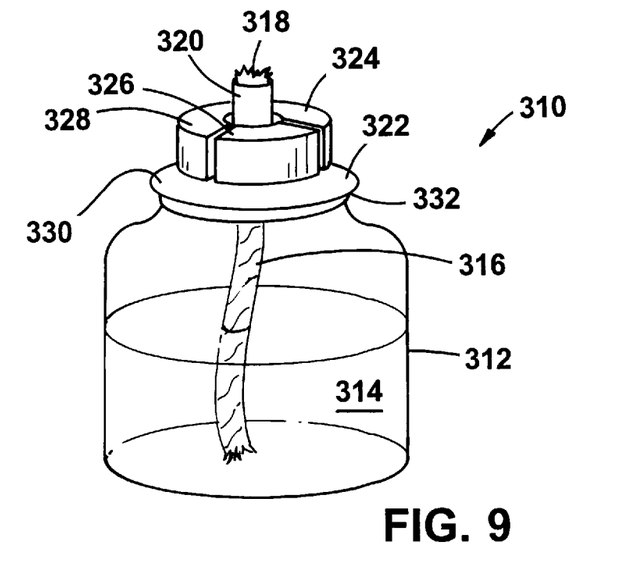

FIG. 9 illustrates a yet further embodiment with plural emanator elements according to the invention. As is shown thereon, a fragrance delivery device 310 includes a fluid vessel 312 contains a quantity of a fuel 314 therein, a wick 316 having one end intended to be burned 318, said wick passing upward through a center post part 320 which includes a self-supporting rigid casing element 322. As may be seen in FIG. 9, the casing element 322 includes a flat-based portion 330 which extends inwardly from an outward peripheral margin 332 and although not shown joins at the base of the center post portion 320. As may be seen, a plurality of emanator elements 324, 326, 328 may be placed proximate to the burning end of the wick 318 such that when it is ignited, they are sufficiently heated that the fragrance material, may be volatilized and delivered to an ambient environment. Similar to the advantages of the plural emanator elements as described above in FIG. 8, the plural emanator elements 324, 326, 328 may be similarly provided with different fragrance materials, as well as other volatile materials. Again, as they are simultaneously heated during the operation of the fragrance-delivery device 310, their individual volatile materials may be volatilized and delivered to an ambient environment such as a closed room.

Figure 10:
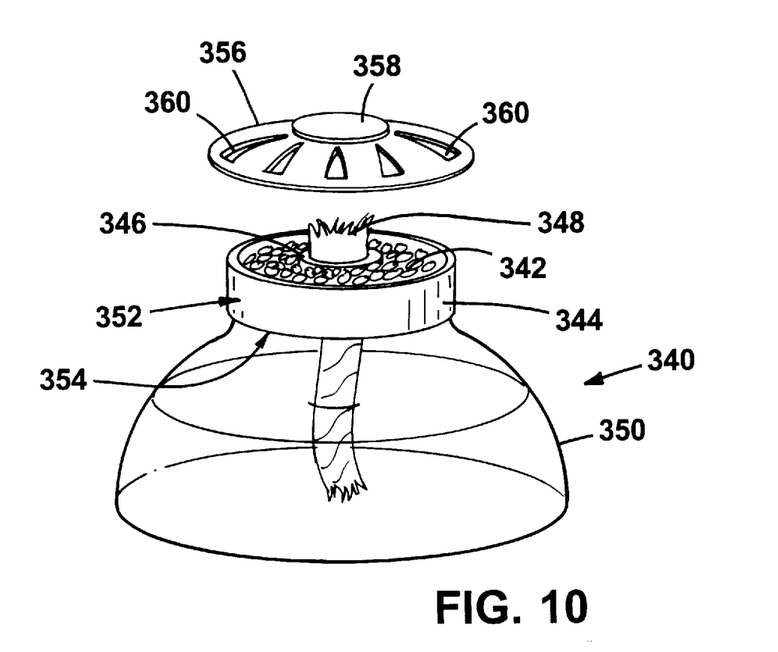
FIG. 10 illustrates an embodiment with bead shaped emanator elements.

Turning now to FIG. 10 there is illustrated an embodiment of a fragrance delivery device 340 according to the invention which includes as an emanator element a plurality of individual comminuted emanator elements in the form of beads 342. As has been discussed previously, each of the individual comminuted emanator elements 342 are impregnated with a quantity of a fragrance material, or other material, as described above. As is illustrated in FIG. 10, they may be mixed with further comminuted fragrancing elements 342 which may contain the same, or different fragrance materials. In such a manner, a mixture of comminuted fragrancing elements 342 may be provided to the fragrance-delivery device 340. These comminuted emanator elements may be of any shape, whether a regular geometrical solid (cube, rectangle, sphere, etc.) or may be of non-regular geometrical shape such as ground or broken irregular pieces of a porous ceramic material, as well as ground, chopped, or pelletized non-ceramic porous materials. Desirably, each of these comminuted emanator elements 342 are less than one centimeter in their maximum dimensions, and are, however, preferably with in the range of between about 0.1 centimeter–0.8 centimeter, and even more preferably are between 0.1 centimeter–0.6 centimeter. Smaller sizes than those preferred have attendant handling problems by a consumer as they may become powdery, while at the same time, sizes in excess of 1 centimeter are not convenient in their use.

While it is contemplated that these comminuted emanator elements 342 may be used solely with a fluid vessel containing a quantity of a fuel and a wick, such comminuted emanator elements 342 are conveniently utilized with a self-supporting rigid casing element 344. Such casing element may be formed of a foil or metallic particle containing film as has been discussed generally in conjunction with FIG. 4J. Similarly here, the casing element 344 includes the center post portion 346 which is adapted to retain a portion of the wick 348 passing therethrough and extending upwardly from a fluid vessel 350. The casing element 344 further includes a side wall portion 352 which is located annularly apart from the center post portion 346 as well as a bottom 354 extending between the side wall portion 352 to the center post portion 346. Both the side wall portion 352 and the center post portion 356 depend from the bottom 354 and extend upwardly therefrom, and thereby defining an annular trough having a "U"-shaped cross section which is suitably dimensioned to contain a quantity of the comminuted emanator elements 342 within.

In use, the consumer merely provides a quantity of comminuted emanator elements 342 within the interior of the casing element 344 and generally distributes them evenly within. The wick may then be ignited.

Optionally, but in certain cases desirably, there is further included a casing element cap 356 having a first passage 358 therethrough which is adapted to permit the passage of at least the wick end 348. Further, desirably are included a plurality of passages 360 also be a screen, but desirably are slits which permit the volatized fragrance material from the comminuted emanator elements 342 to pass therethrough, yet denying the passage of the comminuted elements 342 themselves. Conveniently, such a casing element cap 356 is placed upon the casing 344 to cover the annular trough. Such may be simply placed on, or may include any variety of fastening means, such as peripheral clips, mating screw threads or friction fitting a portion of the cap 356 with a portion of the casing element 344.

By means of the use of any of the fragrance delivery devices according to the invention and described herein, a delightful fragrancing effect may be provided to an environment such as a room, or other area in need of fragrancing. In accordance with such a process, there is provided a delivery device such as has been hereuntofore described. Said device is placed within the room or other environment and when it is not ignited, the slowly diffusing fragrance material volatilizes from the emanator element and thus provides a fragrancing effect to the environment. When the fragrance device's wick is ignited and a flame burns, consequent heating of the emanator element enhances the vapor delivery rate and the evaporation of the fragrance material from the interior of the emanator element.

While it is described in the specification as useful and the provision of fragrancing material such as perfumes and/or the like; it is to be clearly understood that the delivery devices according to the invention may be useful in providing other volatilizable materials to the environment including, for example, insect repellents, and/or disinfecting compositions.

Each fragrance device according to the invention may be used as a "single use" type device whereby it is provided in a pre-packaged form with the fluid vessel which may, but need not be, pre-filled with a quantity of fuel, an emanator element, wick, and (when provided) a wick holder tube. Such may be preassembled or may be simply assembled by the consumer from the constituent parts. In such a single use scenario, the fragrance device is utilized in any of the manners described above and when the fuel is consumed and/or most all of the fragrance material has already been delivered from the emanator element, the whole delivery device may be discarded. In an alternative, however, the fuel may be replenished and the fragrance device reused. Similarly, when all or some of the fragrance has been already vaporized from the emanator element, it too may be replenished by immersing it in a volume of a fragrance, and the thus replenished emanator element may be returned to the device, and the fragrance device may be reused virtually indefinitely. Also, the emanator element may be replenished without removing it from the fragrance device. Thus, the reuse of the delivery device particularly with different fragrances and/or different volatile materials is specifically contemplated.

We claim:

1. A delivery device for the controlled release of a volatile substance which comprises:

a fluid vessel having a neck end, wherein said fluid vessel contains a quantity of fuel, said fuel comprising at least one organic liquid;

a porous emanator element having a flat face contacting the neck end of the fluid vessel, and a central passage, said emanator having entrained within a quantity of a volatile liquid;

a wick having a first end adapted to be ignited, and a second end in contact with the fuel, said first end passing completely through the emanator element passage; and a wick holding tube passing through the emanator element passage and encasing at least part of the wick, wherein the outer diameter of at least a portion of the wick is substantially the same as the inner diameter of at least a portion of the wick holder, and the outer diameter of at least a portion of the wick holder is substantially the same as the inner diameter of at least a portion of the emanator element passage.

2. The delivery device according to claim 1 wherein the emanator element comprises a porous ceramic material impregnated with a volatile liquid.

3. The delivery device according to claim 2 wherein the emanator element is faced on one or more sides with a metal foil or metallic particle containing film.

4. The delivery device according to claim 2 wherein the emanator element further includes a casing element.

5. The delivery device according to claim 4 wherein the casing element is a self-supporting casing element.

6. The delivery device according to claim 1 wherein the emanator element includes a non-ceramic porous material.

7. The delivery device according to claim 6 wherein the emanator element comprises a porous polymeric material impregnated with a volatile liquid.

8. The delivery device according to claim 6 wherein the non-ceramic porous material is paper.

9. The delivery device according to claim 6 wherein the non-ceramic porous material is a woven or non-woven textile material.

10. The delivery device according to claim 6 wherein the non-ceramic porous material is a fibrous substance.

11. The delivery device according to claim 6 wherein the non-ceramic porous material is a foamed polymeric material.

12. The delivery device according to claim 6 wherein the emanator element further includes a casing element.

13. The delivery device according to claim 12 wherein the casing element is a self-supporting casing element.

14. The delivery device according to claim 1 wherein the emanator element is a plurality of emanator elements.

15. The delivery device according to claim 1 wherein the emanator element is a plurality of comminuted emanator elements.

16. The delivery device according to claim 1 wherein the volatile liquid is a fragrance material.

17. The delivery device according to claim 1 wherein the volatile liquid is an insect repellent composition.

18. The delivery device according to claim 1 wherein the volatile liquid is a deodorizing composition.

19. The delivery device according to claim 1 wherein the volatile liquid is a medicinal compound.

20. The delivery device according to claim 1 wherein the volatile liquid is an herbal composition.

21. The delivery device according to claim 1 wherein the volatile liquid is a disinfectant composition.

22. The delivery device according to claim 1 which further comprises a chimney.

23. A process for delivering a volatile liquid to an ambient environment which includes the step of:

providing a delivery device according to claim 1; and, igniting the wick and heating the emanator element.

24. A process for simultaneously delivering a first and a second volatile liquid to an ambient environment which includes the steps of:

providing a delivery device according to claim 14 having a first emanator element impregnated with said first volatile liquid, and, a second emanator element impregnated with said second volatile liquid; and, igniting the wick and heating the emanator elements.

25. A process for sequentially delivering a first and a second volatile liquid to an ambient environment which includes the steps of:

providing a delivery device according to claim 1 having a first emanator element impregnated with said first volatile liquid, and, a second emanator element impregnated with said second volatile liquid; and, igniting the wick and heating said first emanator element for a first time interval; and, substituting said first emanator element with said second emanator element and heating for a second time interval.

* * * * *